(12) United States Patent
Wang et al.

(10) Patent No.: US 11,119,056 B2
(45) Date of Patent: Sep. 14, 2021

(54) MINIATURE TEMPERATURE-CONTROLLED TRIAXIAL TESTER FOR TESTING UNSATURATED SOIL SUITABLE FOR MICRO-COMPUTED TOMOGRAPHY (CT) SCANNING AND METHOD THEREBY

(71) Applicant: Shandong University, Shandong (CN)

(72) Inventors: Jipeng Wang, Shandong (CN); Jiyuan Luan, Shandong (CN); Taiheng Liu, Shandong (CN); Yiran Tan, Shandong (CN)

(73) Assignee: Shandong University, Shandong (CN)

( * ) Notice: Subject to any disclaimer, the term of this patent is extended or adjusted under 35 U.S.C. 154(b) by 0 days.

(21) Appl. No.: 16/998,747

(22) Filed: Aug. 20, 2020

(65) Prior Publication Data
US 2021/0055234 A1 Feb. 25, 2021

(30) Foreign Application Priority Data

Aug. 22, 2019 (CN) .......................... 201910778356.0

(51) Int. Cl.
*G01N 23/00* (2006.01)
*G01N 23/046* (2018.01)
(Continued)

(52) U.S. Cl.
CPC .......... *G01N 23/046* (2013.01); *G01N 23/083* (2013.01); *G01N 23/10* (2013.01); *G01N 2223/616* (2013.01)

(58) Field of Classification Search
CPC ........................ G01N 2223/616; G01N 23/046
See application file for complete search history.

(56) References Cited

U.S. PATENT DOCUMENTS

| 2018/0259467 A1* | 9/2018 | Buono | G01N 23/046 |
| 2019/0178820 A1* | 6/2019 | Weiss | G01B 21/042 |

FOREIGN PATENT DOCUMENTS

| CN | 202661405 U | 1/2013 |
| CN | 202676633 U | 1/2013 |

(Continued)

OTHER PUBLICATIONS

Chinese Office Action dated Mar. 20, 2020 for Chinese Application No. 201910778356.0.

*Primary Examiner* — Dani Fox
(74) *Attorney, Agent, or Firm* — EIP US LLP

(57) ABSTRACT

A miniature temperature-controlled triaxial tester for testing unsaturated soil suitable for micro-computer tomography (CT) scanning and a method thereby. The triaxial tester includes a device body, where the bottom of the device body is fixed on a base, and the top of the device body is provided with a strain control device. The device body includes a vertically arranged polymethyl methacrylate shell, a PMMA inner cover is nested inside the PMMA shell, and a vacuum gap is formed between the PMMA shell and the PMMA inner cover; a pressure cell is formed by a space defined by the PMMA inner cover, a sample accommodating area for accommodating a test sample is arranged in the pressure cell, a heating element is arranged below the sample accommodating area and connected to a temperature control device, and a temperature sensor is arranged inside the PMMA inner cover and connected to a receiver.

18 Claims, 2 Drawing Sheets

(51) Int. Cl.
*G01N 23/083* (2018.01)
*G01N 23/10* (2018.01)

(56) References Cited

FOREIGN PATENT DOCUMENTS

| | | |
|---|---|---|
| CN | 103424414 A | 12/2013 |
| CN | 104614256 A | 5/2015 |
| CN | 106198578 A | 12/2016 |
| CN | 206583829 U | 10/2017 |
| CN | 207181328 U | 4/2018 |
| CN | 108844980 A | 11/2018 |
| CN | 208505928 U | 2/2019 |
| CN | 109443928 A | 3/2019 |
| CN | 109738294 A | 5/2019 |

* cited by examiner

MINIATURE TEMPERATURE-CONTROLLED TRIAXIAL TESTER FOR TESTING UNSATURATED SOIL SUITABLE FOR MICRO-COMPUTED TOMOGRAPHY (CT) SCANNING AND METHOD THEREBY

CROSS-REFERENCE TO RELATED APPLICATIONS

This application is a claims priority to Chinese Application No. 201910778356.0, filed Aug. 22, 2019, under 35 U.S.C. § 119(a). The above-referenced patent application is incorporated by reference in its entirety.

BACKGROUND OF THE INVENTION

Technical Field

The present disclosure belongs to the technical field of mechanics research of unsaturated soil, and particularly relates to a miniature temperature-controlled triaxial tester for testing unsaturated soil suitable for micro-computer tomography (CT) scanning and a method thereby.

Description of the Related Technology

The micro-CT scanning technology can effectively help analyze and study an internal structure of a material because of its nondestructive characteristics, and has been widely used in various fields. With the rapid development of CT, noninvasive research on geotechnical materials has become popular in recent years, and the CT technology has a great impact on the research field of unsaturated soil. X-ray CT scanning has been used to study the microscopic characteristics of unsaturated granular materials.

At present, micro-CT usually uses X-ray to penetrate through a sample for scanning, and is assisted with an application system of a high-performance computer to reconstruct an internal image of the sample. Theoretically, the intensity of X-ray after penetrating the sample is measured by a specific detector, and an attenuation coefficient of each volume unit is different in each projection direction. At the same time, the scanning among an X-ray source, the sample and the detector is completed, so as to obtain complete data needed to reconstruct a CT image, and then a cross-sectional image can be reconstructed according to a certain image reconstruction algorithm.

When the micro-CT scanning technology is used, in order to obtain higher resolution, as can be seen according to its technical characteristics, the focus size of ray beam should be reduced, but this will limit the penetration ability of ray; the size of the sample should be controlled and it should be ensured that the sample rotates stably during a scanning period, but this will limit the dimension of a scanned object. Such restrictions greatly affect the study of micro-characteristics of unsaturated granular materials.

A conventional device for experiments of unsaturated soil has two problems. One is that the device includes metal parts, and the other is that the size of the device is excessively large for the X-ray CT technology. The metal parts have a great impact on penetrability of X-ray, and the excessively large sample size affects the imaging resolution, thereby affecting the accuracy during three-phase microstructure reconstruction. With respect to a conventional test device, an external test is performed and then an unsaturated sample after the test is taken out of the device and put into an micro-CT scanning room for CT scanning. It is found that in the process of transferring soil samples after the external test, structural disturbance inevitably occurs to the soil samples. This affects test results, and makes test accuracy low. Moreover, once the triaxial test is completed, the condition of the test samples cannot be adjusted.

SUMMARY

In order to overcome the shortcomings of the prior art, the present disclosure provides a miniature temperature-controlled triaxial tester for testing unsaturated soil suitable for micro-CT scanning. The triaxial tester can suspend the loading of a test sample under different suction (different saturation), different temperatures and different stresses and strains and perform CT scanning at the same time, thereby obtaining a microstructure and a three-phase distribution evolution law of unsaturated soil under triaxial shear. Based on the relationship with the measured stresses and strains in a macroscopic aspect, the impact of microstructure changes and liquid distribution evolution on macroscopic mechanical properties can be obtained.

A first objective of the present disclosure is to provide a miniature temperature-controlled triaxial tester for testing unsaturated soil suitable for micro-CT scanning. To achieve the objective, the present disclosure uses the following technical solutions:

A miniature temperature-controlled triaxial tester for testing unsaturated soil suitable for micro-CT scanning, including a device body, where the bottom of the device body is fixed on a base, and the top of the device body is provided with a strain control device;

the device body includes a vertically arranged polymethyl methacrylate (PMMA) shell, a PMMA inner cover is nested inside the PMMA shell, and a vacuum gap is formed between the PMMA shell and the PMMA inner cover; a pressure cell is formed by a space defined by the PMMA inner cover, a sample accommodating area for accommodating a test sample is arranged in the pressure cell, a heating element is arranged below the sample accommodating area and connected to a temperature control device, and a temperature sensor is arranged inside the PMMA inner cover and connected to a receiver.

Further, the top and the bottom of the sample accommodating area corresponding to the test sample are provided with porous stones, the top porous stone is connected to a pore air pressure channel, and the bottom porous stone is connected to a pore water pressure channel.

Further, the top of the top porous stone is a first PMMA body, and the bottom of the bottom porous stone is a second PMMA body.

Further, the heating element is a heating wire which is wound and arranged outside the second PMMA body.

Further, the top of the first PMMA body is a PMMA top cap, and the bottom of the second PMMA body is a PMMA bottom cap.

Further, the top of the PMMA top cap is connected to a loading end of the strain control device, and an immersed force sensor is arranged outside the loading end of the strain control device and connected to the receiver.

Further, the bottom of the pressure cell is connected to a confining pressure applying device.

Further, the PMMA shell and the PMMA inner cover each have a cylindrical structure, and the PMMA shell and the PMMA inner cover have minimum diameters at positions close to the sample accommodating area.

A second objective of the present disclosure is to provide a test method using the triaxial tester for testing unsaturated soil described above, which includes the following steps of:

placing the foregoing triaxial tester for testing unsaturated soil on a rotating table of an micro-CT scanning room, aligning an X-ray source of micro-CT with a test sample, loading the test sample with axial strain under different suction, different temperatures and different confining pressures, suspending the loading at different strain stages and performing CT scanning at the same time; rotating the rotating table by 360° and scanning at different angles to obtain sliced gray images, and obtaining a microstructure, three-phase distribution and an evolution law of each intersecting interface of unsaturated soil under shear by analyzing the images and the test process.

A third objective of the present disclosure is to provide a test method using the triaxial tester for testing unsaturated soil described above, which includes the following steps of:

placing a prepared test sample at a sample accommodating area, fixing a high-temperature-resistant PMMA top cap and a high-temperature-resistant PMMA bottom cap respectively and hooping and sealing the PMMA top cap and the PMMA bottom cap with O rings to prevent water from permeating;

applying vacuum to the test sample through a pore water pressure channel by a vacuum pump, and keeping a pore air pressure channel closed, where this operation can keep the vertical state of the test sample when different parts are assembled, and is also beneficial to the saturation process of the sample;

applying a confining pressure to the test sample through a pressure cell, opening the pore water pressure channel to allow water to flow into the pressure cell to saturate the test sample, and opening the pore air pressure channel to the atmosphere;

after the test sample is saturated, applying a corresponding pore air pressure and pore water pressure;

fixing the triaxial tester for testing unsaturated soil on a rotating table of an micro-CT scanning chamber, performing strain loading, suspending the loading at different strain stages, and then performing CT scanning; and rotating the rotating table by 360° and scanning at different angles to obtain sliced gray images, and obtaining a microstructure, three-phase distribution and an evolution law of each intersecting interface of unsaturated soil under shear by analyzing the images and the test process.

The present disclosure has the following beneficial effects:

1. As a PMMA shell and a PMMA inner cover of the triaxial tester according to the present disclosure are each made of transparent PMMA, the triaxial tester can be directly placed in an micro-CT scanning room for testing. CT scanning can be performed after the loading is suspended at different stages in the testing process, such that images of unsaturated soil under triaxial shear can be obtained immediately, with no need to transfer the sample after the loading and then scan again. Thus, this improves the accuracy of the whole test.

2. Compared with a conventional triaxial tester for testing unsaturated soil, the triaxial tester according to the present disclosure adds temperature field control and stress-strain control. This can be used to study the coupling direction of temperature-stress-deformation, and can meet various and comprehensive requirements of the test.

3. The triaxial tester according to the present disclosure overcomes the limitations and shortcomings of the conventional triaxial testing of unsaturated soil, and is combined with the micro-CT scanning technology. This provides a new idea for the study of the microscopic property mechanism of unsaturated soil under different temperature conditions.

4. The triaxial tester according to the present disclosure can improve the resolution of CT scanning images when applied under certain micro-CT power.

5. Compared with the conventional triaxial tester for testing unsaturated soil, the triaxial tester according to the present disclosure has a much smaller size, is easy to carry and can be reused.

BRIEF DESCRIPTION OF THE DRAWINGS

The accompany drawings of the specification constituting a part of the present application provide further understanding of the present application. The schematic examples of the present application and description thereof are intended to be illustrative of the present application and do not constitute an undue limitation of the present application.

Figure 1:
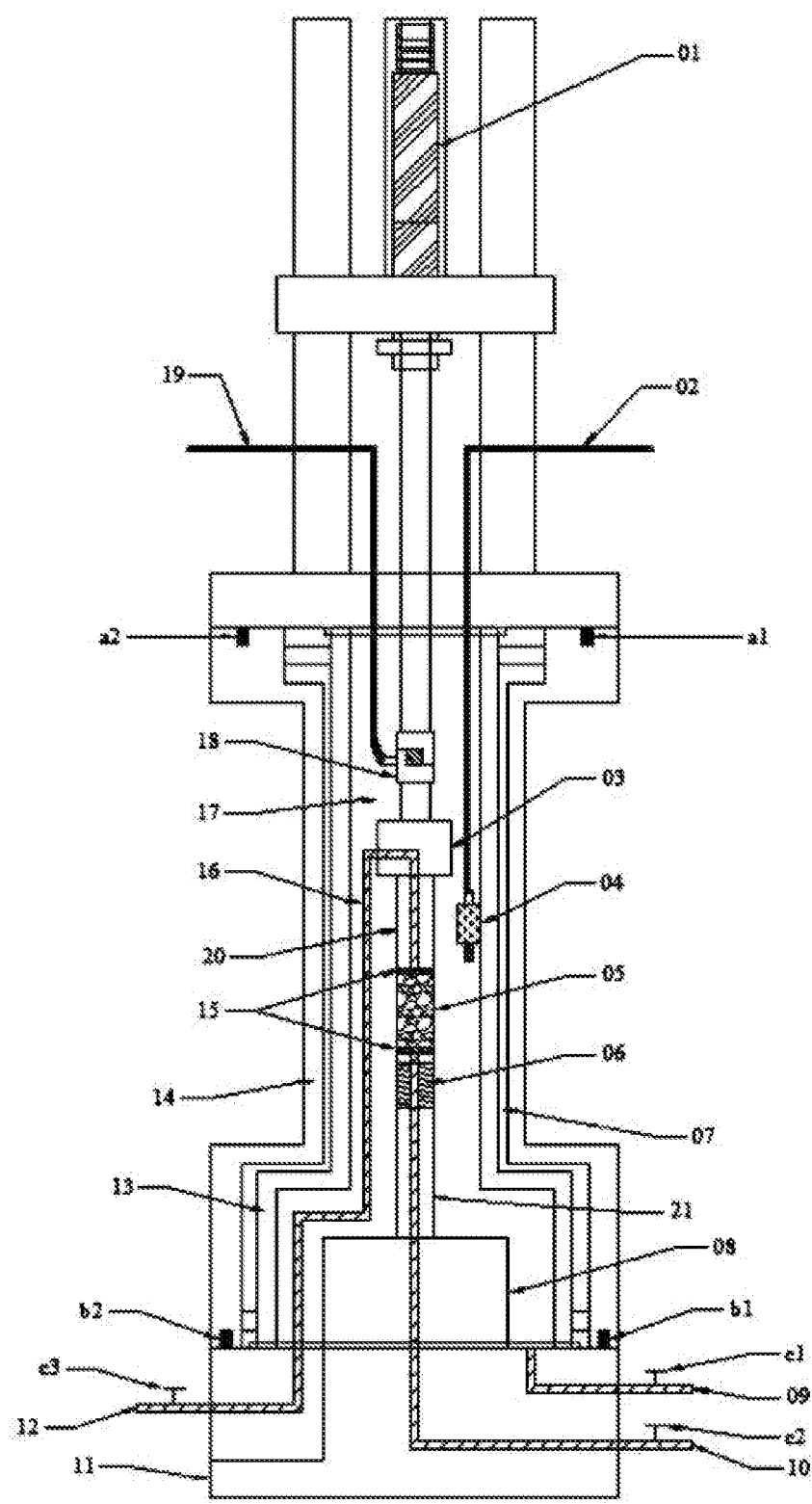
FIG. 1 is a schematic structural diagram of a triaxial tester for testing unsaturated soil suitable for micro-CT scanning.

In the figure: 01. stepping motor, 02. temperature sensor cable, 03. PMMA top cap, 04. temperature sensor, 05. test sample, 06. heating wire, 07. vacuum layer, 08. PMMA bottom cap, 09. porous confining pressure channel, 10. pore water pressure channel, 11. base, 12. pore air pressure channel, 13. PMMA inner cover, 14. PMMA shell, 15. porous stone, 16. silica gel conduit, 17. pressure cell, 18. immersed force sensor, 19. force sensor cable, 20. first PMMA body, 21. second PMMA body;

a1. top bolt, a2. top bolt, b1. bottom bolt, b2. bottom bolt;

c1. control valve, c2. control valve, c3. control valve;

1a. X-ray source, 1b. scanning sample, 1c. rotating table, 1d. X-ray receiver.

DETAILED DESCRIPTION OF CERTAIN INVENTIVE EMBODIMENTS

It should be noted that the following detailed description is exemplary and aims to further describe the present application. Unless otherwise specified, all technical and scientific terms used herein have the same meaning as commonly understood by one of ordinary skill in the technical field to which the present application belongs.

It should be noted that the terms used herein are merely used for describing the specific implementations, but are not intended to limit exemplary implementations of the present application. As used herein, the singular form is also intended to include the plural form unless otherwise indicated obviously from the context. Furthermore, it should be further understood that the terms "include" and/or "comprise" used in this specification specify the presence of features, steps, operations, devices, components and/or a combination thereof.

For convenience of description, if the words "up", "down", "left" and "right" appear in the present disclosure, they only mean that they are consistent with the up, down, left and right directions of the accompanying drawing itself, and do not limit the structure. They are only for convenience of describing the present disclosure and simplifying the description, but do not indicate or imply that referred devices or elements must have a specific orientation and be constructed and operated in a specific orientation, so they cannot be understood as a limitation to the present disclosure.

As introduced in the background, it is found that in the process of transferring soil samples after an external test, structural disturbance inevitably occurs to the soil samples. This affects test results, and makes test accuracy low. In order to solve the foregoing technical problems, the present application provides a miniature temperature-controlled triaxial tester for testing unsaturated soil suitable for micro-CT scanning. This tester is suitable for micro-CT scanning and can also be combined with triaxial testing of unsaturated soil.

The present application provides a miniature temperature-controlled triaxial tester for testing unsaturated soil suitable for micro-CT scanning, including a device body, where the bottom of the device body is fixed on a base, and the top of the device body is provided with a strain control device.

The device body includes a vertically arranged PMMA shell, a PMMA inner cover is nested inside the PMMA shell, and a vacuum gap is formed between the PMMA shell and the PMMA inner cover; a pressure cell is formed by a space defined by the PMMA inner cover, a sample accommodating area for accommodating a test sample is arranged in the pressure cell, a heating element is arranged below the sample accommodating area and connected to a temperature control device, and a temperature sensor is arranged inside the PMMA inner cover and connected to a receiver.

Example 1

The triaxial tester disclosed by this example is further described below with reference to the FIGS. 1 to 2.

Referring to FIG. 1, the miniature temperature-controlled triaxial tester for testing unsaturated soil suitable for micro-CT scanning includes a metal base 11, a porous confining pressure channel 09 (with a diameter of 2-4 mm), a pore water pressure channel 10 (with a diameter of 2-4 mm), a pore air pressure channel 12 (with a diameter of 2-4 mm), a lower high-temperature-resistant PMMA bottom cap 08 (with a diameter of 50 mm), a middle high-temperature-resistant PMMA shell 14 and a high-temperature-resistant PMMA inner cover 13, a pressure cell 17, a vacuum layer 07 capable of performing heat insulation on a temperature field, a heating wire 06, a temperature sensor 04 capable of monitoring the temperature of the temperature field where a sample is located, an upper PMMA top cap 03, an immersed force sensor 18 capable of monitoring axial stress on the sample and a top stepping motor 01 capable of converting an electric pulse signal into displacement deformation. The stepping motor is supported by a metal bracket and connected to the PMMA shell 14 by a bolt.

The metal base 11 is connected to the PMMA shell 14 of the device body through a bottom bolt b1 and a bottom bolt b2. The device body is connected to the metal bracket of the stepping motor 01 through a top bolt a1 and a top bolt a2.

The PMMA inner cover 13 is nested in the PMMA shell 14, and the vacuum layer 07 formed by a gap is formed between the PMMA inner cover 13 and the PMMA shell 14, which uses the vacuum heat insulation principle to perform heat insulation on the temperature field where the sample is located. The pressure cell 17 is formed by a space defined by the PMMA inner cover 13, the PMMA bottom cap 08 is disposed on a lower portion inside the pressure cell 17, and the PMMA top cap 03 is disposed on an upper portion thereof. A sample accommodating area for placing a test sample 05 is arranged between the PMMA top cap 03 and the PMMA bottom cap 08. The top and the bottom of the test sample 05 are provided with porous stones 15. The top of the top porous stone 15 is the first PMMA body 20, and the bottom of the bottom porous stone 15 is a second PMMA body 21. The PMMA top cap 03 is arranged at the top of the first PMMA body 20, and the PMMA bottom cap 08 is arranged at the bottom of the second PMMA body 21. The bottom of the PMMA bottom cap 08 is fixed to the base 11, and the top of the PMMA top cap 03 is connected to a loading end (i.e., an output shaft thereof) of the stepping motor 01. The periphery of the test sample 05 at the sample accommodating area is not blocked by other structures, and is in direct contact with a cavity of the pressure cell 17. The test sample is filled with water through the pressure cell 17 by a confining pressure applying device, so that a confining pressure is applied. The PMMA top cap 03 and the PMMA bottom cap 08 each have a diameter greater than that (10 mm) of the sample accommodating area.

The PMMA shell 14 and the PMMA inner cover 13 each have a cylindrical structure. The two have minimum diameters at positions close to the sample accommodating area. That is, middle portions of the PMMA shell 14 and the PMMA inner cover 13 are closer to the sample accommodating area, so that the penetration of CT scanning rays is better and the CT scanning imaging is more accurate. The diameter (the minimum external diameter of 60 mm and the minimum internal diameter of 50 mm) of the PMMA shell is greater than that (the minimum external diameter of 45 mm and the minimum internal diameter of 35 mm) of the PMMA inner cover. The PMMA shell can protect the device body, and if the micro-CT power is certain, the imaging resolution is higher when the sample is scanned.

The pore air pressure channel 12 is connected into the pressure cell 17 of the device body through a silica gel conduit 16 and communicated with the top porous stone 15, and the pore water pressure channel 10 is also connected into the device body through a silica gel conduit and communicated with the bottom porous stone 15. The silica gel conduit 16 has an external diameter of 6 mm and an internal diameter of 4 mm. The porous confining pressure channel 09 is introduced into the pressure cell 17 and communicated with the bottom of the pressure cell 17. The pore air pressure channel 12, the pore water pressure channel 10 and the porous confining pressure channel 09 each have a diameter of 4 mm. The pore air pressure channel 12 is provided with a control valve c3, the pore water pressure channel 10 is provided with a control valve c2, and the porous confining pressure channel 09 is provided with a control valve c1.

The test sample 05 is an unsaturated soil sample with a diameter of 10 mm and a height of 20 mm. The size of the sample is smaller than that for a conventional device, which is suitable for a CT scanning system and is beneficial to obtaining better resolution to explore the microstructure of the sample.

As the PMMA shell 14, the PMMA inner cover 13, the PMMA top cap 03 and the PMMA bottom cap 08 are each made of the transparent PMMA, an X-ray source for micro-CT scanning can directly pass through the test sample for imaging. Since the PMMA can allow the X-ray to pass through, it is ensured that the resolution of the sample image is not affected when the device performs CT scanning, and it can also be ensured that the device has certain strength. The whole device is a cylinder in appearance, and the diameter and the height of each part are different.

The porous confining pressure channel 09 is connected to the confining pressure applying device, and a confining pressure is applied to the test sample 05 through the porous confining pressure channel 09. The pore air pressure channel 12 is connected to a pore air pressure loading device, and a pore air pressure is applied to the test sample 05 through the pore air pressure channel 12. The pore water pressure channel 10 is connected to a pore water pressure loading device, and a pore water pressure is applied to the test sample 05 through the pore water pressure channel 10. The stepping motor 01 is the strain control device of this triaxial tester, and an electric pulse signal is converted into displacement deformation through the stepping motor 01 to control the strain of the test sample. The confining pressure applying device, the pore air pressure loading device and the pore water pressure loading device all adopt the prior art in the field of mechanics research on unsaturated soil, which is not repeated here.

The heating wire 06 is a heating element of this device and is connected to a temperature control device. The heating wire 06 is wound around the outside of a high-temperature-resistant second PMMA body 21 and heats water filled in the pressure cell 17. The requirements for insulation and the like of the heating wire 06 can be adjusted according to the specific situation, and the specific insulation operation can be done by using the prior art. The temperature sensor 04 is arranged in the pressure cell 17 and disposed on an inner side wall of the PMMA inner cover 13. The top of the temperature sensor 04 is connected to a receiver through a temperature sensor cable 02, and the receiver is connected to the temperature control device. Through the arrangement of the heating wire 06 and the temperature sensor 04, the temperature of the whole tester can be controlled, thus controlling the temperature of the temperature field where the sample is located. The immersed force sensor 18 is arranged outside the loading end of the stepping motor 01 above the sample accommodating area. The immersed force sensor 18 can also be arranged in other positions inside the pressure cell 17. The top of the immersed force sensor 18 is connected to the receiver through a force sensor cable 19, and the receiver is connected to a controller and records data. The immersed force sensor can reduce measurement errors (under the action of piston friction) of axial stress, making the measurement more accurate. The signal transmission and control between the temperature sensor 04, the immersed force sensor 18, the receiver and the controller is performed by the prior art, which is not described in detail here.

Figure 2:
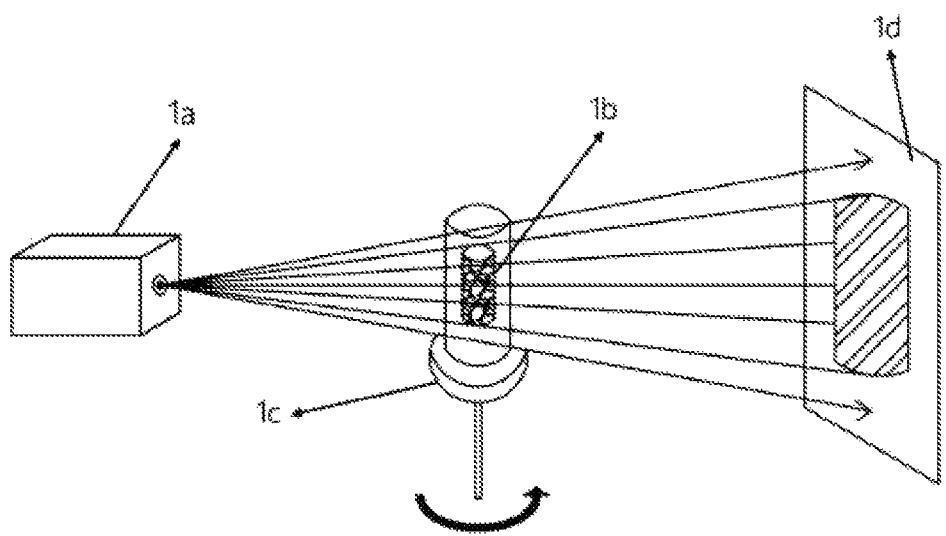
FIG. 2 is an operating schematic diagram of an micro-CT scanning system.

As shown in FIG. 2, when the miniature temperature-controlled triaxial tester for testing unsaturated soil by cooperating with the micro-CT scanning system, the device assembled according to the process is installed on a rotating table 1c of micro-CT, and an X-ray source 1a of micro-CT is aligned with a scanned sample 1b of a PMMA body of the device. Then, a triaxial path load is applied, the loading can be suspended under different suction (different saturation), different temperatures and different stresses and strains, and CT scanning can be performed at the same time. The rays emitted by the X-ray source 1a penetrate through the sample, and an X-ray receiver 1d receives the rays that have penetrated through the sample. The rotating table rotates by 360°, so that the sample can be scanned at different angles to obtain sliced gray images. Since the penetration rates of X-rays are different for various substances in the sample, the gray values of the substances are different. After scanning, images with different gray values can be obtained, which can be assisted with an application system of a high-performance computer to reconstruct internal images of the sample. Finally, a microstructure, three-phase distribution and an evolution law of each intersecting interface of an unsaturated granular material under triaxial shear can be obtained by analyzing the images and the test process.

The miniature temperature-controlled triaxial tester for testing unsaturated soil suitable for micro-CT scanning according to the present disclosure can control the saturation state and suction value of a sample, and can perform dehumidification and moisture absorption cyclic cycle. The device is small in size and favorable for operating on the rotating table of micro-CT. The triaxial path load is applied. The loading can be suspended under different suction (different saturation), different temperatures and different stresses and strains and CT scanning is performed at the same time, thereby obtaining a microstructure, three-phase distribution and an evolution law of each intersecting interface of unsaturated soil under shear. This improves the resolution of CT scanning images, realizes the combination of the micro-CT scanning technology and triaxial testing of unsaturated soil, can improve the test efficiency, and can meet various and comprehensive requirements of the test.

The test sample 05 described in this example is a rock-soil sample, or may be other types of unsaturated particle samples. This example takes the rock-soil sample as an example for testing, and the specific testing method of the tester provided by the present disclosure is specifically explained.

Specifically, a certain amount of qualified soil samples or other granular materials are selected, and the test sample 05 is prepared in a cylindrical (with a diameter of 10 mm) latex film. The test sample has a diameter of 10 mm and a length of 20 mm. Two porous stones 15 with a diameter of 10 mm are placed above and below the test sample respectively. After being filled, a die is placed at a sample accommodating area, a high-temperature-resistant PMMA top cap 03 and a high-temperature-resistant PMMA bottom cap 08 are fixed respectively and hooped and sealed with O rings to prevent water from permeating. Before the cylindrical die is removed, vacuum is applied in the test sample through a pore water pressure channel 10 by a vacuum pump, and a pore air pressure channel 12 is kept closed. This operation can keep the test sample vertical when different parts are assembled, and is also beneficial to the saturation process of the sample.

The periphery of the test sample 05 is a pressure cell, and the pressure cell is connected to a confining pressure applying device through a porous confining pressure channel 09 and can apply different confining pressures in a triaxial test device.

After the device is assembled, a certain confining pressure is applied to the test sample by the confining pressure applying device through the porous confining pressure channel 09. Then the pore water pressure channel 10 is closed and connected to a water container; and then the pore water pressure channel 10 is opened to allow water to flow into the pressure cell 17 to saturate the test sample 05, and the pore air pressure channel 12 is open to the atmosphere. After water saturation, a pore air pressure is applied through the pore air pressure channel 12, and a pore water pressure is applied through the pore water pressure channel 10 (using an axis translation technology, the difference between the air pressure and the water pressure and suction for a matrix).

The miniature triaxial tester is fixed on a rotating table 1c in a microfocus X-ray CT scanning room for CT scanning. When the axial load stops, scanning is performed at different strain stages to keep an axial piston at a fixed position, and the loading speed should be slow enough to maintain the condition of complete drainage.

After images with different gray values are obtained, an application system of a high-performance computer is used for assistance to reconstruct internal images of the sample. A three-dimensional numerical matrix can be generated by combining gray value images which are cut horizontally per pixel. The matrix can be separated into three phases by a program written based on Matlab, and the shape and area of each intersection surface can be obtained.

The above describes the specific examples of the present disclosure with reference to the accompanying drawings, but is not intended to limit the protection scope of the present disclosure. Those skilled in the art should understand that various modifications or transformations made by those skilled in the art without creative efforts based on the technical solutions of the present disclosure still fall within the protection scope of the present disclosure.

The above is merely preferred examples of the present application and is not intended to limit the present application, and various changes and modifications can be made to the present application by those skilled in the art. Any modification, equivalent replacements, improvement, and the like made within the spirit and principle of the present application should fall within the protection scope of the present application.

What is claimed is:

1. A miniature temperature-controlled triaxial tester for testing unsaturated soil suitable for industrial computer tomography (CT) scanning, comprising a device body, wherein the bottom of the device body is fixed on a base, and the top of the device body is provided with a strain control device;

the device body comprises a vertically arranged polymethyl methacrylate (PMMA) shell, a PMMA inner cover is nested inside the PMMA shell, and a vacuum gap is formed between the PMMA shell and the PMMA inner cover; a pressure cell is formed by a space defined by the PMMA inner cover, a sample accommodating area for placing a test sample is arranged in the pressure cell, a heating element is arranged below the sample accommodating area and connected to a temperature control device, and a temperature sensor is arranged inside the PMMA inner cover and connected to a receiver;

the test sample has a smaller size than traditional equipment;

the strain control device is a stepping motor, which converts an electrical pulse signal into a displacement deformation signal, to control the strain of the test sample; an immersed force sensor is placed outside the loading end of the stepping motor above the sample accommodating area; and the top and the bottom of the sample accommodating area corresponding to the test sample are provided with porous stones; the top of the top porous stone is provided with a first PMMA body, and the bottom of the bottom porous stone is provided with a second PMMA body; and the heating element is a heating wire which is wound and arranged outside the second PMMA body, to heat the water in the pressure cell.

2. The triaxial tester for testing unsaturated soil according to claim 1, wherein the top and the bottom of the sample accommodating area corresponding to the test sample are provided with porous stones, the top porous stone is connected to a pore air pressure channel, and the bottom porous stone is connected to a pore water pressure channel.

3. The triaxial tester for testing unsaturated soil according to claim 1, wherein the top of the first PMMA body is provided with a PMMA top cap, and the bottom of the second PMMA body is provided with a PMMA bottom cap.

4. The triaxial tester for testing unsaturated soil according to claim 3, wherein the top of the PMMA top cap is connected to the loading end of the strain control device, and the immersed force sensor is arranged outside the loading end of the strain control device and connected to the receiver.

5. The triaxial tester for testing unsaturated soil according to claim 1, wherein the bottom of the pressure cell is connected to a confining pressure applying device.

6. The triaxial tester for testing unsaturated soil according to claim 1, wherein the PMMA shell and the PMMA inner cover each have a cylindrical structure, and the PMMA shell and the PMMA inner cover have minimum diameters at positions close to the sample accommodating area.

7. A test method using the triaxial tester for testing unsaturated soil according to claim 1, comprising the following steps of:

placing the triaxial tester for testing unsaturated soil on a rotating table of an industrial CT scanning room, aligning an X-ray source of industrial CT with a test sample, loading the test sample with axial strain under different suction, different temperatures and different confining pressures, suspending the loading at different strain stages and performing CT scanning at the same time; rotating the rotating table by 360° and scanning at different angles to obtain sliced gray images, and obtaining a microstructure, three-phase distribution and an evolution law of each intersecting interface of unsaturated soil under shear by analyzing the images and the test process.

8. The test method according to claim 7, wherein the top and the bottom of the sample accommodating area corresponding to the test sample are provided with porous stones, the top porous stone is connected to a pore air pressure channel, and the bottom porous stone is connected to a pore water pressure channel.

9. The test method according to claim 7, wherein the top of the first PMMA body is provided with a PMMA top cap, and the bottom of the second PMMA body is provided with a PMMA bottom cap.

10. The test method according to claim 9, wherein the top of the PMMA top cap is connected to the loading end of the strain control device, and the immersed force sensor is arranged outside the loading end of the strain control device and connected to the receiver.

11. The test method according to claim 7, wherein the bottom of the pressure cell is connected to a confining pressure applying device.

12. The test method according to claim 7, wherein the PMMA shell and the PMMA inner cover each have a cylindrical structure, and the PMMA shell and the PMMA inner cover have minimum diameters at positions close to the sample accommodating area.

13. A test method using the triaxial tester for testing unsaturated soil according to claim 1, comprising the following steps of:

placing a prepared test sample at a sample accommodating area, fixing a PMMA top cap and a PMMA bottom cap respectively and hooping and sealing the PMMA top cap and the PMMA bottom cap with O rings;

applying vacuum to the test sample through a pore water pressure channel by a vacuum pump, and keeping a pore air pressure channel closed;

applying a confining pressure to the test sample through a pressure cell, opening the pore water pressure channel to allow water to flow into the pressure cell to saturate the test sample, and opening the pore air pressure channel to the atmosphere;

after the test sample is saturated, applying a corresponding pore air pressure and pore water pressure;

fixing the triaxial tester for testing unsaturated soil on a rotating table of an industrial CT scanning chamber, performing strain loading, suspending the loading at different strain stages, and then performing CT scanning; and rotating the rotating table by 360° and scanning at different angles to obtain sliced gray images, and obtaining a microstructure, three-phase distribution and an evolution law of each intersecting interface of unsaturated soil under shear by analyzing the images and the test process.

14. The test method according to claim 13, wherein the top and the bottom of the sample accommodating area corresponding to the test sample are provided with porous stones, the top porous stone is connected to a pore air pressure channel, and the bottom porous stone is connected to a pore water pressure channel.

15. The test method according to claim 13, wherein the top of the first PMMA body is provided with a PMMA top cap, and the bottom of the second PMMA body is provided with a PMMA bottom cap.

16. The test method according to claim 15, wherein the top of the PMMA top cap is connected to the loading end of the strain control device, and the immersed force sensor is arranged outside the loading end of the strain control device and connected to the receiver.

17. The test method according to claim 13, wherein the bottom of the pressure cell is connected to a confining pressure applying device.

18. The test method according to claim 13, wherein the PMMA shell and the PMMA inner cover each have a cylindrical structure, and the PMMA shell and the PMMA inner cover have minimum diameters at positions close to the sample accommodating area.

* * * * *